(12) United States Patent
Schmitz et al.

(10) Patent No.: US 7,618,448 B2
(45) Date of Patent: Nov. 17, 2009

(54) POLYMERIC, DEGRADABLE DRUG-ELUTING STENTS AND COATINGS

(75) Inventors: Klaus-Peter Schmitz, Rostock-Warnemünde (DE); Detlef Behrend, Rostock-Warnemünde (DE); Katrin Sternberg, Rostock (DE); Niels Grabow, Rostock (DE); David P. Martin, Arlington, MA (US); Simon F. Williams, Sherborn, MA (US)

(73) Assignee: Tepha, Inc., Lexington, MA (US)

( * ) Notice: Subject to any disclaimer, the term of this patent is extended or adjusted under 35 U.S.C. 154(b) by 299 days.

(21) Appl. No.: 11/671,632

(22) Filed: Feb. 6, 2007

(65) Prior Publication Data

US 2007/0185561 A1 Aug. 9, 2007

Related U.S. Application Data

(60) Provisional application No. 60/747,144, filed on May 12, 2006, provisional application No. 60/765,840, filed on Feb. 7, 2006, provisional application No. 60/765,808, filed on Feb. 7, 2006.

(51) Int. Cl.
*A61F 2/06* (2006.01)
(52) U.S. Cl. .................... 623/1.46; 427/2.24
(58) Field of Classification Search ....... 623/1.15–1.49; 523/124; 264/400; 427/2.1–2.24
See application file for complete search history.

(56) References Cited

U.S. PATENT DOCUMENTS

| | | | |
|---|---|---|---|
| 5,059,211 A | 10/1991 | Stack | |
| 5,306,286 A | 4/1994 | Stack | |
| 5,527,337 A | 6/1996 | Stack | |
| 5,629,077 A | 5/1997 | Turnlund | |
| 5,670,161 A | 9/1997 | Healy et al. | |
| 5,766,710 A | 6/1998 | Turnlund | |
| 5,811,272 A | 9/1998 | Snell et al. | |
| 5,935,506 A * | 8/1999 | Schmitz et al. | 264/400 |
| 6,045,568 A | 4/2000 | Igaki et al. | |
| 6,245,537 B1 | 6/2001 | Williams et al. | |
| 6,316,262 B1 | 11/2001 | Huisman et al. | |

(Continued)

FOREIGN PATENT DOCUMENTS

EP 0 770 401 5/1997

(Continued)

OTHER PUBLICATIONS

Colombo, et al., "Biodegradable stents: "fulfilling the mission and stepping away".", *Circulation*, 102(4):371-3 (2000).

(Continued)

*Primary Examiner*—Suzette J Gherbi
(74) *Attorney, Agent, or Firm*—Pabst Patent Group LLP

(57) ABSTRACT

Absorbable stents and absorbable stent coatings have been developed with improved properties. These devices preferably comprise biocompatible copolymers or homopolymers of 4-hydroxybutyrate, and optionally poly-L-lactic acid and other absorbable polymers and additives. Compositions of these materials can be used to make absorbable stents that provide advantageous radial strengths, resistance to recoil and creep, can be plastically expanded on a balloon catheter, and can be deployed rapidly in vivo. Stent coatings derived from these materials provide biocompatible, uniform coatings that are ductile, and can be expanded without the coating cracking and/or delaminating and can be used as a coating matrix for drug incorporation.

46 Claims, 3 Drawing Sheets

U.S. PATENT DOCUMENTS

| | | |
|---|---|---|
| 6,323,010 B1 | 11/2001 | Skraly et al. |
| 6,368,436 B1 | 4/2002 | Canet et al. |
| 6,548,569 B1 * | 4/2003 | Williams et al. ............ 523/124 |
| 6,719,934 B2 | 4/2004 | Stinson |
| 6,991,647 B2 | 1/2006 | Jadhav |
| 6,997,948 B2 | 2/2006 | Stinson |
| 7,011,678 B2 | 3/2006 | Tenerz et al. |
| 7,179,883 B2 * | 2/2007 | Williams et al. ............ 528/354 |
| 7,268,205 B2 * | 9/2007 | Williams et al. ............ 528/354 |
| 7,445,628 B2 * | 11/2008 | Ragheb et al. ............ 623/1.42 |
| 2001/0029398 A1 | 10/2001 | Jadhav |
| 2003/0069629 A1 | 4/2003 | Jadhav |
| 2003/0211131 A1 | 11/2003 | Martin et al. |
| 2004/0193241 A1 | 9/2004 | Stinson |
| 2004/0260386 A1 | 12/2004 | Shalaby |
| 2005/0137678 A1 | 6/2005 | Varma |
| 2006/0018948 A1 | 1/2006 | Guire |
| 2006/0129222 A1 | 6/2006 | Stinson |
| 2007/0185561 A1 * | 8/2007 | Schmitz et al. ............ 623/1.15 |

FOREIGN PATENT DOCUMENTS

| | | |
|---|---|---|
| WO | WO 98/51812 | 11/1998 |
| WO | WO 99/32536 | 7/1999 |
| WO | WO 00/56376 | 9/2000 |
| WO | WO 02/059201 | 8/2002 |
| WO | WO 2007/092417 | 8/2007 |

OTHER PUBLICATIONS

Erne, P. et al., "The road to bioabsorbable stents: reaching clinical reality?" *Cardiovasc Intervent Radiol.* 29(1):11-6(2006).

Grabow, et al., "Mechanical properties of laser cut poly(L-lactide) micro-specimens: implications for stent design, manufacture, and sterilization", *J. Biomech. Eng.*, 127(1):25-31 (2005).

Hori, et al., "Chemical synthesis of high molecular weight poly(3-hydroxybutyrate-co-4-hydroxybutyrate)" *Polymer* 36(24):4703-4705 (1995).

Laaksovirta, et al., "Encrustation and strength retention properties of the self-expandable, biodegradable, self-reinforced L-lactide-glycolic acid co-polymer 80:20 spiral urethral stent in vitro ", *J. Urol.*, 170(2 Pt 1):468-71 (2003).

Martin, et al., "Medical applications of poly-4-hydroxybutyrate: a strong flexible absorbable biomaterial", *Biochem. Eng. J.*, 16:97-105 (2003).

Nebeker, et al., "Hypersensitivity cases associated with drug-eluting coronary stents: a review of available cases from the Research on Adverse Drug Events and Reports (RADAR) project", *J. Am. Coll. Cardiol.*, 47(1):175-81 (2006).

Ormiston, et al. , First-in-human implantation of a fully bioabsorbable drug-eluting stent: the BVS poly-L-lactic acid everolimus-eluting coronary stent, *Catheter Cardiovasc. Interv.*, 69(1):128-31 (2007).

Salu, et al., "Drug-eluting stents: a new treatment in the prevention of restenosis. Part I: Experimental studies", *Acta Cardiol.*, 59(1):51-61 (2004).

Shaw et al., "Encrustation of biomaterials in the urinary trac," *Urol Res.* 33(1):17-22(2005).

Sousa, et al., "New frontiers in cardiology: drug-eluting stents: Part I", *Circulation*, 107(17):2274-9 (2003).

Sousa, et al., "New frontiers in cardiology: drug-eluting stents: Part II", *Circulation*, 107(18):2383-9 (2003).

Steinbüchel, "Polyhydroxyalkanoic acids", *Biomaterials*, 123-213 (1991).

Steinbüchel, at al.,"Diversity of Bacterial Polyhydroxyalkanoic Acids", *FEMS Microbial. Lett.*, 128:219-228 (1995).

Sternberg, et al., "Bioartificial materials in urology", *Urologe A*, 43(10):1200-7 (2004).

Tamai, et al., "Initial and 6-month results of biodegradable poly-l-lactic acid coronary stents in humans", *Circulation*, 102(4):399-404 (2000).

Tanguay, at al.,"Current status of biodegradable stents", *Cardiol. Clin.*, 12(4):699-713 (1994).

Van Der Giessen, et al., Marked inflammatory sequelae to implantation of biodegradable and nonbiodegradable polymers in porcine coronary arteries, *Circulation*, 94(7):1690-7 (1996).

Virmani, at al., "Drug-eluting stents: caution and concerns for long-term outcome", *Coron. Artery Dis.*, 15(6):313-8 (2004).

Williams, at al. Applications of PHAs in Medicine and Pharmacy, in Biopolymers, *Polyesters, Ill* vol. 4:91-127 (2002).

Zeltinger, at al.,"Advances in the Devlopment of Cornoary Stints" *Biomaterials Forum*, 2004 First Quarter, 8, 9 and 24. (2004).

* cited by examiner

POLYMERIC, DEGRADABLE DRUG-ELUTING STENTS AND COATINGS

CROSS-REFERENCE TO RELATED APPLICATIONS

The present application claims priority to U.S. Ser. No 60/747,144 filed May 12, 2006, U.S. Ser. No. 60/765,840, filed Feb. 7, 2006, and U.S. Ser. No. 60/765,808 filed Feb. 7, 2006.

FIELD OF THE INVENTION

The present invention generally relates to absorbable polymer compositions that can be used to prepare absorbable stents, and absorbable stent coatings.

BACKGROUND OF THE INVENTION

Stents are currently used in a range of medical applications normally to prevent re-occlusion of a vessel after a procedure to dilate the vessel. Examples include cardiovascular, urology, and gastroenterology stents, with the former being by far the largest market. Generally, stents are made from permanent materials, such as metal alloys or non-absorbable thermoplastics, and can additionally incorporate special coatings and drugs to improve their performance in vivo. These coatings, for example, include a number of polymer coating materials for metallic stents, as well as a variety of active agents, such as agents that are anti-inflammatory or immunomodulators, antiproliferative agents, agents which affect migration and extracellular matrix production, agents which affect platelet deposition or formation of thrombis, and agents that promote vascular healing and re-endothelialization. Notably the coatings of currently marketed stents are made from permanent materials.

While the incorporation of certain active agents in coatings on the surfaces of coronary metal stents has been demonstrated to retard restenosis, it has been reported that the polymer coatings that are left after elution of the drug can present a serious risk of late thrombosis (Virmani, R et al., Coron Artery Dis. 2004;15(6):313-8). It has also been reported that the polymeric coating materials of drug-eluting stents may cause hypersensitivity reactions in the patient treated with such coated stents (Nebeker, J. R. et al., J Am Coll Cardiol 2006:47:175-81). Thus, there is a need to develop new stent coating materials that can be used to deliver drugs without the risk of late thrombosis and hypersensitivity reactions.

Furthermore, although permanent metal stents are used widely in coronary stenting applications, and their use in peripheral stenting is growing rapidly, there remain several drawbacks to the use of permanent materials to manufacture these stents (Colombo, A et al., Circulation. 2000 25:102(4): 371-3, Erne, P. et al., Cardiovasc Intervent Radiol. 2005). First, metal stents are not compatible with certain methods of medical imaging, such as MRI and CT scanning systems. Second, metal stents can cause complications if the patient subsequently needs coronary artery bypass surgery, or other surgical intervention, requiring manipulation of a stented vessel. Third, the use of permanent stents can result in long-term compliance mismatches between the metal stent and the stented vessel, and fourth, in certain peripheral applications, catastrophic failure of metal stent struts has been reported.

It should also be noted that permanent stents used in urology applications to temporarily relieve obstruction in a variety of benign, malignant, and post-traumatic vessel conditions are prone to rapid encrustation (Shaw G. L. et al., Urol Res. 2005 Feb;33(1):17-22). Such encrustation often necessitates removal of the stent. Removal, however, requires an additional procedure, and can be difficult and painful because of tissue in-growth. The use of a degradable implant would eliminate this clinical problem.

To address the disadvantages associated with the use of permanent materials in stents and stent coatings, there have been several reports describing the use of absorbable materials to make stents and stent coatings. U.S. Pat. Nos. 5,059,211 and 5,306,286 to Stack et al. describe the use of absorbable materials to make stents. Stack, however, does not describe which specific absorbable materials a person skilled in the art would use to make an absorbable stent, or the properties necessary to make such stents.

U.S. Pat. No. 5,935,506 to Schmitz et al. describes a method to manufacture an absorbable stent from poly-3-hydroxybutyrate (P3HB).

U.S. Pat. No. 6,045,568 to Igaki et al. describes absorbable stents manufactured from knitting yarns of polyactic acid (PLA), polyglycolic acid (PGA), polyglactin (P(GA-co-LA)), polydioxanone (PDS), polyglyconate (a block co-polymer of glycolic acid and trimethylene carbonate, P(GA-co-TMC)), and a copolymer of glycolic acid or lactic acid with ε-caprolactone (P(GA-co-CL) or P(LA-co-CL)).

Laaksovirta et al. describe a self-expandable, biodegradable, self-reinforced stent from P(GA-co-LA) for use in urethral applications (J Urol. 2003 Aug;170(2 Pt 1):468-71).

The potential use of polyanhydride and polyorthoester polymers to manufacture absorbable stents has also been described by Tanguay, J. F. et al. Current Status of Biodegradable stents, Cardiology Clinics, 12:699-713 (1994).

WO 98/51812 to Williams et al. discloses methods to remove pyrogens from polyhydroxyalkanoates, and the fabrication of stents with these depyrogenated materials. WO 99/32536 to Martin et al. and WO 00/56376 to Williams et al. disclose methods to prepare polyhydroxyalkanoates with controlled degradation rates, and the fabrication of stents with these materials.

Van der Giessen et al. (Marked Inflammatory Sequelae to Implantation of Biodegradable and Nonbiodegradable Polymers in Porcine Coronary Arteries, Circulation, 94:1690-1697 (1996)) evaluated coatings of a copolymer of glycolic acid and lactic acid (P(GA-co-LA)), polycaprolactone (PCL), poly-3-hydroxybutyrate-co-3-hydroxyvalerate (P(3HB-co-3HV), a polyorthoester, and a polyethyleneoxide-polybutylene terephthalate on metal stents, and reported that the coatings induced marked inflammatory reactions within the coronary artery.

Despite some progress towards the development of absorbable stents and stent coatings, there is currently no coronary or peripheral stent device comprising an absorbable material approved for general sale in the United States or Europe. This is partly because of the highly demanding requirements of an absorbable material used for medical stenting applications and the shortcomings of the currently available materials. Further improvements to existing materials that are considered desirable, or required, include the following elements: (i) an absorbable stent or stent coating that is biocompatible, does not create a risk of late stage thrombosis, and provides long-term vessel patency; (ii) an absorbable stent that has sufficient radial strength (or hoop strength) to prevent the collapse of the vessel wall or stent; (iii) an absorbable polymer composition that when processed into a stent or stent coating can be expanded in vivo, from a suitably low profile form to the desired diameter without surface or strut cracking or similar types of mechanical failure; (iv) an absorbable stent or permanent stent coated with an absorbable polymer that can be dilated sufficiently fast in vivo to allow deployment of the stent without risk to the patient, and using a reasonable inflation pressure, if the stent is delivered using a balloon catheter; (v) an absorbable stent that does not recoil significantly after deployment; (vi) an absorbable stent that is sufficiently resistant to creep to be effective; (vii) an absorbable stent with strut thicknesses that are relatively low in profile once the stent is implanted, and with edges that are smooth; (viii) an absorbable stent coating that can be applied in a uniform manner, without defects such as web formation between struts, and a method for such application; (iv) an absorbable stent, and/or a stent coated with an absorbable material, where the struts are not susceptible to fracture after implantation, and the risk of vessel perforation is eliminated; (x) an absorbable stent that does not interfere with medical scanning systems, such as MRI and CT; (xi) an absorbable stent, and a stent coated with an absorbable material, that protects against an inflammatory response, limits smooth muscle cell proliferation, and neointimal hyperplasia after implantation, stimulates positive remodeling of the vessel wall, and eliminates long-term compliance mismatches between the stent and the vessel wall; (xii) an absorbable stent, and/or a stent coated with an absorbable material, that is sufficiently flexible to allow delivery to the desired location without strut fracture or kinking, which can conform to the shape of the affected body lumen; (xiii) an absorbable stent that contains a contrast agent; radiopaque markers, or similar material that allows the stent to be imaged using conventional scanning techniques, (xiv) an absorbable coating that adheres sufficiently strongly to a metal stent, maintains its integrity following stent expansion and does not delaminate; (xv) an absorbable stent and a coated permanent stent that can be loaded with one or more drugs or co-drugs (for example, on the inside or surface of the stent or coating) to improve the performance of the stent by controlled delivery of the drug(s), including agents that are anti-inflammatory or immunomodulators, antiproliferative agents, drugs which affect migration and extracellular matrix production, drugs which affect platelet deposition or formation of thrombis, and drugs that promote vascular healing and re-endothelialization, and that also allow larger drug loadings; (xvi) an absorbable stent and/or a stent coated with an absorbable material that can be mounted onto a catheter, and subsequently delivered in vivo without causing damage to the stent; (xvii) an absorbable stent, and an absorbable coating on a stent, that is absorbed in vivo over a time period that allows positive remodeling of the vessel wall, does not prematurely fail due to fatigue, and results in long-term vessel patency; (xviii) an absorbable stent that does not shorten in an undesirable manner upon expansion and deployment (xix) an absorbable stent or permanent stent coated with an absorbable material that can be sterilized without detrimental loss of properties, for example, by irradiation or exposure to ethylene oxide; (xx) an absorbable stent and a coated metal stent that can be loaded with one or more drugs to improve the performance of the stent by controlled delivery of the drug(s), where the method of polymer degradation (e.g. surface erosion or bulk degradation) allows for delivery of large drugs such as proteins; (xxi) an absorbable stent and a coated permanent stent that can be loaded with one or more drugs to improve the performance of the stent by controlled delivery of the drug(s), where the low-acidity polymer degradation products (of the stent or stent coating) allows for delivery of large drags such as proteins without drug denaturation; (xxii) an absorbable material for use in stents that has a glass transition temperature below body temperature, a melt temperature above 50° C., and a shelf-life of at least one to three years.

It is therefore an object of this invention to provide absorbable compositions that can be used to develop improved absorbable stents, and absorbable stent coatings.

It is another object of this invention to provide improved absorbable stents, and stents coated with absorbable materials.

It is a further object of this invention to provide methods for preparing improved absorbable stents and stents coated with absorbable materials.

It is a yet still further object of this invention to provide methods for the delivery of the absorbable stents and stents coated with absorbable materials.

SUMMARY OF THE INVENTION

Absorbable compositions and stents, and absorbable coatings for stents, with improved properties and performance, and methods for making these materials and devices, have been developed. These compositions and devices are preferably derived from a biocompatible homopolymer and/or copolymer(s) of 4-hydroxybutyrate, and combinations of these materials with other absorbable materials. Absorbable stents are most preferably derived from compositions comprising a homopolymer or copolymer(s) of 4-hydroxybutyrate with a polymer of lactic acid, with or without plasticizers.

Different methods may be used to apply the absorbable stent coatings. Most preferably, the coatings are applied from solution by spraying. Different methods may be used to prepare the absorbable stents. A preferred method comprises forming a tube by solution dipping or extrusion, injection molding or micro injection molding, and cutting the tube with a laser to form the stent. The stent may be used as manufactured or expanded in vivo, for example, using an expandable balloon catheter.

The absorbable stent coatings provide devices with thin coatings on the stent struts, without the formation of web-like structures between the struts, and stents that can be expanded quickly without the coating cracking, delaminating, or losing its structural integrity. The absorbable stent coatings are biocompatible, degrade to less acidic metabolites by mechanisms that include surface erosion (minimizing the risk of particulate breaking away from the stent surface), elongate up to 1,000% of their original length, adhere to the stent, can be mounted to a catheter and deployed without damage to the coating, degrade over a period of up to about one year, can be sterilized by irradiation or treatment with ethylene oxide, and can be loaded or coated with drugs for controlled release. The stents are flexible, and more pliant with the vessel wall; have sufficient radial strength and strength retention to permit positive remodeling for long-term patency; and have a radial recoil of less than 10%, and more preferably less than 6%; can be expanded rapidly in vivo, without cracking or other mechanical failure, preferably in less than five minutes, and more preferably in less than one minute, using a balloon pressure of 4 to 16 bar, more preferably 8 bar, and can be delivered to the desired location without strut fracture, kinking, or damage to the vessel wall; do not exhibit any significant creep at 100 mmHg for 7 days, do not shorten significantly upon expansion; can be constructed with smooth strut edges with strut thicknesses of less than 300 μm, more preferably 160 μm or less for coronary applications, and 250-270 μm for peripheral applications; can contain contrast agents, radiopaque markers or similar material to allow the imaging of the stent in vivo, and can also be loaded and/or coated with therapeutic, prophylactic or diagnostic agents, including, but not limited to, agents that are anti-inflammatory or immunomodulators, antiproliferative agents, drugs which affect migration and extracellular matrix production, drugs which affect platelet deposition or formation of thrombis, and drugs that promote vascular healing and re-endothelialization, at low or high drug loadings; can be sterilized, for example, by gamma-irradiation, electron-beam irradiation or ethylene oxide. In the specific case of coronary applications, the absorbable compositions can be used to prepare absorbable stents that can be expanded in vivo from an inner diameter of approximately 1-1.4 mm to 3-4 mm in about one minute. Larger absorbable stents can also be made for use, for example, in peripheral and urology applications. A preferred internal diameter for peripheral applications is 2.0 to 2.8 mm with a wall thickness of 250-270 µm.

DETAILED DESCRIPTION OF THE INVENTION

Absorbable stents and stents coated with absorbable materials have been developed that have improved properties.

I. Definitions

"Poly-4-hydroxybutyrate" as generally used herein means a homopolymer comprising 4-hydroxybutyrate units. It may be referred to herein as P4HB or TephaFLEX® biomaterial (manufactured by Tepha, Inc., Cambridge, Mass.)

"Copolymers of poly-4-hydroxybutyrate" as generally used herein means any polymer comprising 4-hydroxybutyrate with one or more different hydroxy acid units.

"Copolymers of lactic acid" as generally used herein means any polymer comprising lactic acid with one or more different hydroxy acid units.

"Molecular weight" as used herein, unless otherwise specified, refers to the weight average molecular weight (Mw) as opposed to the number average molecular weight (Mn).

"Blend" as generally used herein means a macroscopically homogeneous mixture of two or more different species of polymer.

"Absorbable" or "degradable" as generally used herein means the material is broken down in the body and eventually eliminated from the body.

"Biocompatible" as generally used herein means the biological response to the material or device is appropriate for the device's intended application in vivo. Any metabolites of these materials should also be biocompatible.

II. Compositions

A. Absorbable Polymers

The stents and stent coatings may be formed from absorbable polymers, such as poly-4-hydroxybutyrate (P4HB), and copolymers thereof, such as poly-4-hydroxybutyrate-co-3-hydroxybutyrate (P(4HB-co-3HB)). In a preferred embodiment, the absorbable stents are formed from combinations of P4HB and/or copolymers thereof, with a second absorbable material. A preferred second absorbable material is a polyhydroxy acid, preferably polylactic acid (PLA), and even more preferably poly-L-lactic acid (PLLA) (such as Resomer® L214 available from Boehringer Ingelheim). Copolymers of lactic acid may also be used as the second absorbable material, including copolymers with glycolic acid.

Figure 1:
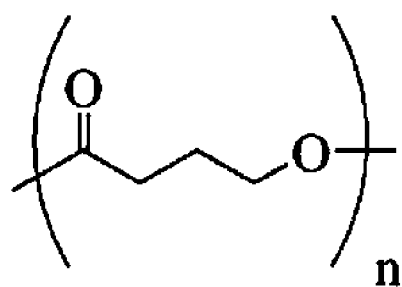
FIG. 1 is the chemical structure of poly-4-hydroxybutyrate (P4HB, TephaFLEX® biomaterial).
Figure 2:
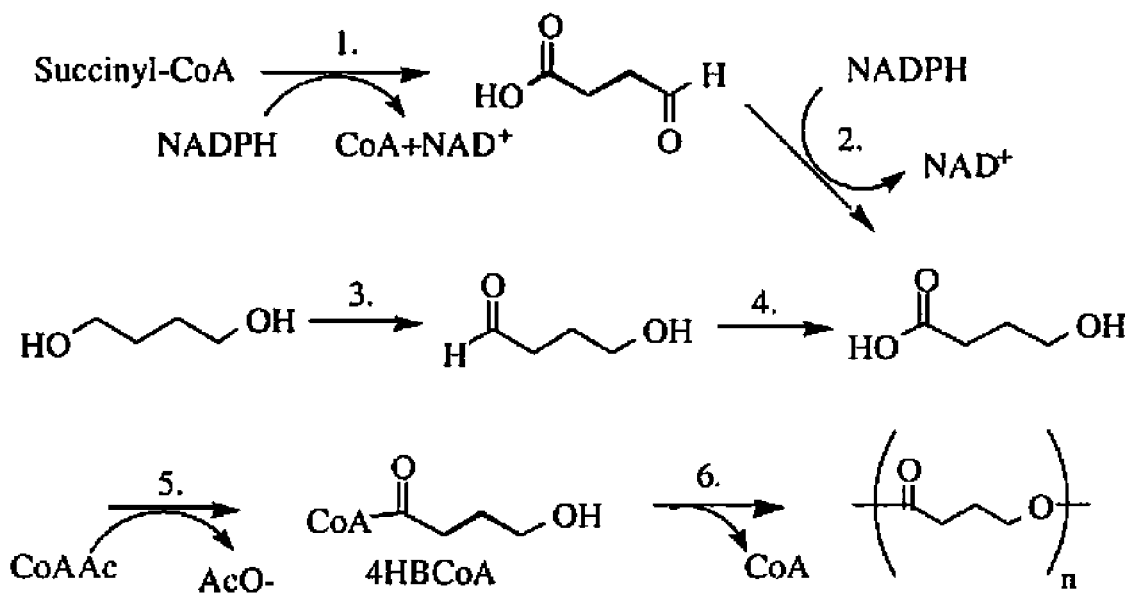
FIG. 2 shows some of the known biosynthetic pathways for the production of P4HB. Pathway enzymes are: 1. Succinic semialdehyde dehydrogenase, 2. 4-hydroxybutyrate dehydrogenase; 3. diol oxidoreductase; 4. aldehyde dehydrogenase; 5. Coenzyme A transferase; and 6. PHA synthetase.

Tepha, Inc. of Cambridge, Mass. produces poly-4-hydroxybutyrate (P4HB) and copolymers thereof using transgenic fermentation methods. Poly-4-hydroxybutyrate is a strong, pliable thermoplastic polyester that is produced by a fermentation process (see U.S. Pat. No. 6,548,569 to Williams et al.). Despite its biosynthetic route, the structure of the polyester is relatively simple (FIG. 1). The polymer belongs to a larger class of materials called polyhydroxy-alkanoates (PHAs) that are produced by numerous microorganisms (Steinbüchel, A. Polyhydroxyalkanoic acid, Biomaterials, 123-213 (1991); Steinbüchel A, et al. Diversity of Bacterial Polyhydroxyalkanoic Acids, FEMS Microbiol. Lett. 128:219-228 (1995); and Doi, Y. Microbial Polyesters (1990)). In nature these polyesters are produced as storage granules inside cells, and serve to regulate energy metabolism. They are also of commercial interest because of their thermoplastic properties, and relative ease of production. Several biosynthetic routes are currently known for producing P4HB, as shown in FIG. 2. Chemical synthesis of P4HB has been attempted, but it has not been possible to produce the polymer with a sufficiently high molecular weight necessary for most applications (Hori, Y., et al. Polymer 36:4703-4705 (1995)).

Tepha, Inc. (Cambridge, Mass.) produces P4HB and related copolymers for medical use, and has filed a Device Master File with the United States Food and Drug Administration (FDA) for P4HB. Related copolymers include 4-hydroxybutyrate copolymerized with 3-hydroxybutyrate or glycolic acid (U.S. patent application publication number US 2003/0211131 by Martin & Skraly, U.S. Pat. No. 6,316,262 to Huisman et al., and U.S. Pat. No. 6,323,010 to Skraly et al.). Tepha has also filed a Device Master File with the United States FDA for copolymers containing 3-hydroxybutyrate and 4-hydroxybutyrate. Methods to control molecular weight of PHA polymers are disclosed by U.S. Pat. No. 5,811,272 to Snell et al., and methods to purify PHA polymers for medical use are disclosed by U.S. Pat. No. 6,245,537 to Williams et al.

PHAs with degradation rates in vivo of less than one year are disclosed by U.S. Pat. No. 6,548,569 to Williams et al. and WO 99/32536 to Martin et al. Other applications of PHAs are reviewed in Williams, S. F., et al., *Polyesters, III*, 4:91-127 (2002), and other applications specific to P4HB are reviewed in Martin et al. Medical Applications of Poly-4-hydroxybutyrate: A Strong Flexible Absorbable Biomaterials, *Biochem. Eng. J.* 16:97-105 (2003).

B. Other Stent Components i. Plasticizers

The absorbable material composition used to produce stents and stent coatings may comprise other materials in addition to the polymers described above. In a preferred method of the invention, a plasticizers may be introduced into the absorbable material prior to forming the stent or stenting coating. Preferred plasticizers are biocompatible. A particularly preferred plasticizer is triethylcitrate (TEC).

ii. Therapeutic, Prophylactic, and Diagnostic Agents

In addition to incorporating plasticizers into the absorbable material, it can be advantageous to incorporate one or more therapeutic, prophylactic or diagnostic agents ("agent") into the stent, either by loading the agent(s) into the absorbable material prior to processing, and/or coating the surface of the stent with the agent(s). The rate of release of agent may be controlled by a number of methods including varying the following the ratio of the absorbable material to the agent, the molecular weight of the absorbable material, the composition of the agent, the composition of the absorbable polymer, the coating thickness, the number of coating layers and their relative thicknesses, and/or the agent concentration. Top coats of polymers and other materials, including absorbable polymers, may also be applied to active agent coatings to control the rate of release. For example, P4HB (TephaFLEX® biomaterial from Tepha, Inc.) may be applied as a top coat on a metallic stent coated with P4HB comprising an active agent, such as rapamycin, to retard the release of rapamycin.

Exemplary therapeutic agents include, but are not limited to, agents that are anti-inflammatory or immunomodulators, antiproliferative agents, agents which affect migration and extracellular matrix production, agents which affect platelet deposition or formation of thrombis, and agents that promote vascular healing and re-endothelialization, described in Tanguay et al. Current Status of Biodegradable Stents, Cardiology Clinics, 12:699-713 (1994), J. E. Sousa, P. W. Serruys and M. A. Costa, Circulation 107 (2003) 2274 (Part I), 2283 (Part II), K. J. Salu, J. M. Bosmans, H. Bult and C. J. Vrints, Acta Cardiol 59 (2004) 51.

Examples of antithrombin agents include, but are not limited to, Heparin (including low molecular heparin), R-Hirudin, Hirulog, Argatroban, Efegatran, Tick anticoagulant peptide, and Ppack.

Examples of antiproliferative agents include, but are not limited to, Paclitaxel (Taxol), QP-2 Vincristin, Methotrexat, Angiopeptin, Mitomycin, BCP 678, Antisense c-myc, ABT 578, Actinomycin-D, RestenASE, 1-Chlor-deoxyadenosin, PCNA Ribozym, and Celecoxib.

Examples of anti-restenosis agents include, but are not limited to, immunomodulators such as Sirolimus (Rapamycin), Tacrolimus, Biorest, Mizoribin, Cyclosporin, Interferon γ1b, Leflunomid, Tranilast, Corticosteroide, Mycophenolic acid and Biphosphonate.

Examples of anti-migratory agents and extracellular matrix modulators include, but are not limited to Halofuginone, Propyl-hydroxylase-Inhibitors, C-Proteinase-Inhibitors, MMP-Inhibitors, Batimastat, Probucol.

Examples of antiplatelet agents include, but are not limited to, heparin.

Examples of would healing agents and endothelialization promoters include vascular epithelial growth factor ("VEGF"), 17β-Estradiol, Tkase-Inhibitors, BCP 671, Statins, nitric oxide ("NO")-Donors, and endothelial progenitor cell ("EPC")-antibodies.

Besides coronary applications, drugs and active agents may be incorporated into the stent or stent coating for other indications. For example, in urological applications, antibiotic agents may be incorporated into the stent or stent coating for the prevention of infection. In gastroenterological and urological applications, active agents may be incorporated into the stent or stent coating for the local treatment of carcinoma.

It may also be advantageous to incorporate in or on the stent a contrast agent, radiopaque markers, or other additives to allow the stent to be imaged in vivo for tracking, positioning, and other purposes. Such additives could be added to the absorbable composition used to make the stent or stent coating, or absorbed into, melted onto, or sprayed onto the surface of part or all of the stent. Preferred additives for this purpose include silver, iodine and iodine labeled compounds, barium sulfate, gadolinium oxide, bismuth derivatives, zirconium dioxide, cadmium, tungsten, gold tantalum, bismuth, platinum, iridium, and rhodium. These additives may be, but are not limited to, mircro- or nano-sized particles or nano particles. Radio-opacity may be determined by fluoroscopy or by x-ray analysis.

III. Methods of Making Absorbable Stents

The stents described herein can be fabricated from solution processes, such as dip coating and casting, melt processes such as extrusion and injection molding, and combinations thereof.

In a preferred method, an absorbable stent may be prepared as follows. A polymer, such as P4HB or copolymer thereof, is optionally mixed in a predetermined ratio with a second absorbable polymer, such as PLLA, and if desired, a plasticizer, such as triethylcitrate (TEC), and/or other additives, in a suitable solvent, to prepare a viscous solution of a predetermined concentration. A rod or mandrel of predetermined diameter is then repeatedly dipped into the viscous solution and removed so as to build up layers of the absorbable material composition on the rod, by precipitation of the material as the solvent is evaporated, with the layer previously deposited only being partially dissolved. Successive dipping of the rod is repeated until the desired thickness of material is built up on the rod, whereupon the rod is withdrawn to yield a circular tube, known as the stent blank, that may be trimmed or coated further as desired.

In an alternative method to prepare the stent blank; a tube of predefined dimensions may be melt extruded from a blend of P4HB or copolymers thereof, optionally with a second absorbable polymer, such as PLLA, and if desired a plasticizer, and/or other additives.

In a further alternative method to prepare the stent blank, a tube of predefined dimensions may be injection molded or micro system injection molded from a blend or composition of P4HB or copolymer thereof with the second absorbable polymer, such as PLLA, and if desired a plasticizer, and/or other additives.

In a preferred method, the dimensions of the stent blank for coronary application are an external diameter of approximately 1.3 mm, and a wall thickness of approximately 150 μm.

The stent blank may then be cut to form the stent. In a preferred method, the stent is cut with a laser according to a predefined stent design. Examples of suitable stent designs are described by Grabow et al. (J Biomech Eng. 2005 Feh; 127(1):25-31) and Sternberge et al. (Uroluge A. 2004 October;43 (10):1200-7). In a preferred embodiment, a $CO_2$ laser, or a femtosecond laser is used to cut the stent blank.

Another alternative method to prepare the stent blank, is to prepare a fiber by injection molding or extrusion of a composition of P4HB or copolymer thereof, optionally with a second absorbable polymer, such as PLLA, and if desired, a plasticizer and/or other additives. The fiber may be reinforced by solid-state drawing. The stent can then be fabricated from a single fiber or multiple fibers, which may be bound, knitted, braided, woven or welded to a tubular structure or to form a tubular structure.

Additives may, if desired, be added to the stent or stent blank at different steps of the fabrication process. Such additives can include radiopaque materials and/or active agents.

Also, stent coatings may be added to the stent after stent fabrication. Such coatings can include radiopaque materials and/or active agents.

Absorbable stents prepared according to these met hods are characterized by the following properties: biocompatability; potentially reduced risk of late stage thrombosis and restenosis; low profile; rapid deployment in vivo; maintenance of structural integrity after expansion; radial strength and strength retention; limited recoil after deployment; resistance to creep; elimination of struts that could potentially fracture over the long-term; radio-opaque, if desired; good compliance match between stent and vessel wall; flexibility and low profile to permit delivery of the stent through small vessels and along restricted and tortuous paths; ability to load drug of choice; ability to positively remodel the vessel wall for long-term patency; compatibility with imaging systems, such as CT and MRI; maintenance of length upon expansion; compatibility with several sterilization options, including gamma-irradiation, electron beam irradiation, and treatment with ethylene oxide; degradation that can include, but is not limited to, surface erosion in addition to bulk degradation; lower acidity degradation products and, ability to dilate the stent in vivo sufficiently quickly to allow the deployment of the stent without risk to the patient, and using only a reasonable amount of pressure;

It is notable in particular that absorbable stents and stent coatings can be plastically deformed at normal body temperature, and in reasonable operative times (for example, less than 5 minutes and more preferably less than 1 minute). They do not require the use of thermo-mechanical expansion or stent designs that rely on the use of non-plastic deformation of the stent. For example, U.S. Pat. No. 5,670,161 to Healy et al. describes biodegradable stents made from copolymers of L-lactide and caprolactone that are not plastically expandable at normal body temperature, but can be expanded by using thermo-mechanical expansion. Attempting to expand these stents (and other stents made from compositions of degradable materials that are not plastically expandable) in one minute or less causes the stents to fracture. Although not wishing to be bound by theory, this may be due to the brittle or glassy characteristics of the stent composition. Tamai et al. Circulation, 2000; (102) 399-404 also describes the need to heat a PLLA stent (the Igaki-Tamai stent) to 50° C. in order to expand the stent in 13 seconds. At normal body temperature expansion is reported to take 20 minutes. Zeltinger et al. Biomaterials Forum, 2004 First Quarter, 8, 9 and 24 reported that the expansion of absorbable stents, prepared for example from polylactides (poly-L-lactic acid), with the use of a heated balloon, represented additional risks to the patient, and reported that these stents have therfore not been commercialized. In one approach to overcome the inability to plastically expand stiff, rigid absorbable polymers, this group employed a new stent design, based upon a slide and lock ratchet mechanism. Thus, prior approaches to develop absorbable stents have sought ways using heat to expand rigid, stiff absorbable polymers or polymer compositions, or to eliminate the need for plastic deformation of the polymer composition by using stent designs, such as slide and ratchet or self-expanding designs that do not require compositions that are plastically expandable. In contrast, the stents made from the compositions described herein can be expanded without the use of heat.

The specific compositions described herein are highly advantageous in permitting the deployment of the stent in vivo for coronary applications in approximately one minute, using a reasonable inflation pressure and at normal body temperature, yet still providing an absorbable stent with high radial strength and strength retention, acceptable recoil and creep, flexibility to contour to the vessel wall, ability to remodel the vessel wall and degrade over time, and all based upon a low profile design. The specific compositions described herein can be designed to degrade more rapidly than stents made from polymers or copolymers comprising lactic acid. For example, Ormiston et al. (Catheter Cardiovasc. interv. 2006; (69) 128-131) has reported that absorbable stents made from poly-L-lactic acid (PLLA) degrade very slowly over a period of 2-3 years. In contrast, a specific composition described herein of PLLA comprising 22% P4HB (TephaFLEX® biomaterial from Tepha, Inc.) can be fabricated into an absorbable stent that degrades much faster. At 48 weeks, less than 20% of the original molecular weight of this blend remains compared to almost 50% for a PLLA-derived stent. The rate of degradation may be further adjusted by manipulation of the percentage of P4HB in the P4HB/PLLA blend.

IV. Method of Coating a Stent with an Absorbable Polymer Composition

In a preferred method, a stent may be coated with an absorbable polymer as follows. A polymer, such as P4HB or copolymer thereof, which may optionally incorporate a second absorbable polymer and/or additives, is dissolved at a known concentration in a volatile solvent. The solution is then sprayed onto the stent to be coated in a uniform manner to provide an even surface coating of the stent. Evaporation of the solvent produces a film coating on the surface of the stent. The process may be repeated to build up the thickness of the coating. The concentration of the solution, application time, drying time, position and rotation of the stent, and number of applications, may be adjusted to create the desired coating thickness, and also to yield a coated stent where the coating only evenly coats the struts, and does not form web structures between struts. Additionally, dip coating or which sintering methods may be used to apply the coating.

Stents coated according to these methods are characterized by the following properties: good biocompatibility; a uniform coating that is maintained upon expansion of the stent, adheres well to the stent surface and does not delaminate or crack upon expansion; a coating that degrades partly by surface erosion, in addition to bulk erosion, and is thus less likely to cause thrombosis as a result of small fragments of coating being released from the stent surface; a coating that is less likely to cause an inflammatory response; a coating that can be loaded with a drug or is compatible with surface coating by a drug and a stent coating that can be sterilized by irradiation or treatment with ethylene oxide.

Due to the ductility and high elongation to break of P4HB, and copolymers thereof, stent coatings derived from these materials, and applied using the methods described herein, form exceptionally good coatings that maintain their structural integrity after stent expansion, as evidenced by SEM (Scanning Electron Microscopy). This is advantageous when compared to more brittle materials of limited ductility and low elongation to break.

V. Stent Deployment

The stents described herein can be deployed in vivo by an means appropriate to their design, such as self-expansion, a combination of self-expansion and balloon-expansion, or balloon-expansion without self-expansion. A preferred method of delivery is to mount the stent onto a balloon catheter, insert the stent system into the body at the desired position for delivery, and expand the balloon in a pressure range of 4 to 16 bar, more preferably 8 bar, to locate the stent against the luminal wall in the desired position.

Due to the greater flexibility, relatively low profile, and small diameters of the absorbable stents described herein, it may be possible to deploy these stents in positions that require navigation of difficult and narrow paths. The stents may be used for coronary, peripheral, urological, gastroenterological, neurological, esophageal and tracheal applications.

The present invention will be further understood by reference to the following non-limiting examples.

EXAMPLES

Example 1

Absorbable Coronary Stent from a Dip-Coated Stent Blank

Polymer tubes with an inner diameter of 1.0 or 1.4 mm were fabricated by dip-coating of stainless steel male comes into a 2% w/w solution of a preferred composition of 70% PLLA (Resomer® L214 from Boehringer Ingelheim Pharma), 20% P4HB (TephaFLEX® biomaterial from Tepha Inc., Mw 300-600K) and 10% TEC in chloroform. The dip-coating procedure was repeated until a mean wall thickness of 160±10 µm of the polymer tubes was achieved. Afterwards, the polymer tubes were removed from the cores and washed twice in methanol and twice in water for 24 h each for solvent removal.

The polymer tubes were then machined with a $CO_2$ laser for the manufacture of balloon-expandable coronary stents with nominal dimensions in the diluted state of 3.0 and 3.5 mm diameter and various lengths from 10-25 mm, as established by SEM.

The stents were deployed with a balloon catheter that was inflated to 8 bar within 1 minute. The stents exhibited a recoil between 2-10% upon balloon deflation and a collapse pressure of 0.3-0.7 bar. In contrast to other material compositions, such as a composition of P3HB, P4HB and TEC, no strut cracking was observed, as established by comparing detailed electron micrographs of struts of an absorbable polymeric stent made from a blend of poly-3-hydroxybutyrate (P3HB), poly-4-hydroxybutyrate (P4HB) and triethylcitrate (TEC) (70/20/10% w/w/w) and from a blend of PLLA, P4HB and TEC (70/20/10% w/w/w) after deployment. In contrast to the P3HB/P4HB/TEC stent, the PLLA/P4HB/TEC stent exhibits no strut cracking. SEM shows cracking of a stent composition of P3HB, P4HB and TEC dilated slowly over 7 minutes, compared to a P4HB, PLLA and TEC composition dilated much more rapidly (in 1 minute) which shows no cracking.

Example 2

Absorbable Coronary Stent from an Extruded Stent Blank

Polymer tubes with an inner diameter of 1.0 or 1.4 mm and a wall thickness of 150 µm were fabricated by extrusion of a preferred composition of 78% PLLA (Resomer® L214 from Boehringer Ingelheim Pharma) and 22% P4HB (TephaFLEX® biomaterial from Tepha Inc., Mw 300-600K).

The polymer tubes were then machined with a $CO_2$ or excimer laser for the manufacture of balloon-expandable coronary stents with nominal dimensions in the dilated state of 3.0 and 3.5 mm diameter and various lengths from 10-25 mm.

Example 3

Absorbable Polymeric Matrix for a Drug-Elating Stent Coating

A 0.3% w/w solution of P4HB (TephaFLEX® biomaterial from Tepha, Inc., Mw 300-600K), in chloroform was prepared. Metallic coronary stents were spray-coated with this solution until a mean coating layer thickness of 15-20 micrometer was achieved. After 24 h storage under vacuum to remove the chloroform, the Stents were mounted on standard balloon catheters and afterwards deployed to a nominal diameter of 3.5 mm. Detailed electron micrographs of metallic stent struts coated with P4HB before and after stent dilation illustrate the smoothness and integrity of the coating before and after balloon expansion.

Example 4

Permanent Drug-Eluting Stent with Absorbable Polymeric Coating Matrix and Incorporated Antiproliferative Immunosuppressant (Low Dose)

A 0.3% w/w solution of P4HB (TephaFLEX® biomaterial from Tepha, Inc. Mw 300-600K) and rapamycin (70/30% w/w, polymer/drug) in chloroform was prepared. Metallic coronary stents were spray-coated with this solution until a mean coating layer thickness of 15-20 micrometer was achieved. After 24 h storage under vacuum to remove the chloroform, the stents were mounted on standard balloon catheters and afterwards deployed to a nominal diameter of 3.5 mm. Rapamycin as the active agent was released from the coating.

Example 5

Permanent Drug-Eluting Stent with Absorbable Polymeric Coating Matrix and Incorporated Antiproliferative Immunosuppressant (High Dose)

A 0.3% w/w solution of P4HB (TephaFLEX® biomaterial from Tepha, Inc. Mw 300-600K) and rapamycin (40/60% w/w, polymer drug) in chloroform was prepared. Metallic coronary stents were spray-coated with this solution until a mean coating layer thickness of 15-20 micrometer was achieved. After 24 h storage under vacuum to remove the chloroform, the stents were mounted on standard balloon catheters and afterwards deployed to a nominal diameter of 3.5 mm. Rapamycin as the active agent was released from the coating.

Example 6

Absorbable Drug-Elating Stent with Incorporated Antiproliferative Immunosuppressant (Low Dow)

Polymer tubes with an inner diameter of 2.8 mm were fabricated by dip-coating of stainless steel male cores into a 2% w/w solution of a preferred composition of 70% PLLA (Resomer® L214 from Boehringer Ingelheim Pharma), 20% P4HB (TephaFLEX® biomaterial from Tepha Inc., Mw 300-600K) and 10% TEC in chloroform. The dip-coating procedure was repeated until a mean wall thickness of 250±20 μm of the polymer tubes was achieved. Afterwards, the polymer tubes were removed from the cores and washed twice in methanol and twice in water for 24 h each for solvent and TEC removal.

The polymer tubes were then machined with a $CO_2$ laser for the manufacture of balloon-expandable peripheral vascular stents with nominal dimensions in the dilated state of 6.0 mm diameter and various lengths from 15-25 mm.

The stents were then spray-coated with a 0.3% w/w solution of P4HB and rapamycin (70:30% w/w, polymer/drug) in chloroform. After 24 h storage under vacuum to remove the chloroform, the stents were mounted on balloon catheters. The stents were deployed to a nominal I.D. of 6.0 mm with a balloon catheter, which was inflated in 8 bar within 1 minute. The stents exhibited a recoil of approximately 5% upon balloon deflation and a collapse pressure greater than 0.6 bar. Rapamycin as the active agent was released from the coating.

Example 7

Absorbable Drug-Elating Stent with Incorporated Antiproliferative Immunosuppressant (high dose)

Polymer tubes with an inner diameter of 2.8 mm were fabricated by dip-coating of stainless steel male cores into a 2% w/w solution of a preferred composition of 70% PLLA (Resomer® L214 from Boehringer Ingelheim Pharma), 20% P4HB (TephaFLEX® biomaterial from Tepha Inc., Mw 300-600K) and 10% TEC in chloroform. The dip-coating procedure was repeated until a mean wall thickness of 250±20 μm of the polymer tubes was achieved. Afterwards, the polymer tubes were removed from the cores and washed twice in methanol and twice in water for 24 h each for solvent and TEC removal.

The polymer tubes were then machined with a $CO_2$ laser for the manufacture of balloon-expandable peripheral vascular stents with nominal dimensions in the dilated state of 6.0 mm diameter and various lengths from 15-25 mm.

The stents were then spray-coated with a 0.3% w/w solution of P4HB and tapamycin (40/60% w/w, polymer/drug) in chloroform. After 24 h storage under vacuum to remove the chloroform, the stents were mounted on balloon catheters. The stents were deployed to a nominal I.D. of 6.0 mm with a balloon catheter which was inflated to 8 bar within 1 minute. The stents exhibited a recoil of approximately 5% upon balloon deflation and a collapse pressure greater than 0.6 bar. Rapamycin as the active agent was released from the coating by diffusion and also supported by the polymer degradation.

Example 8

Figure 3:
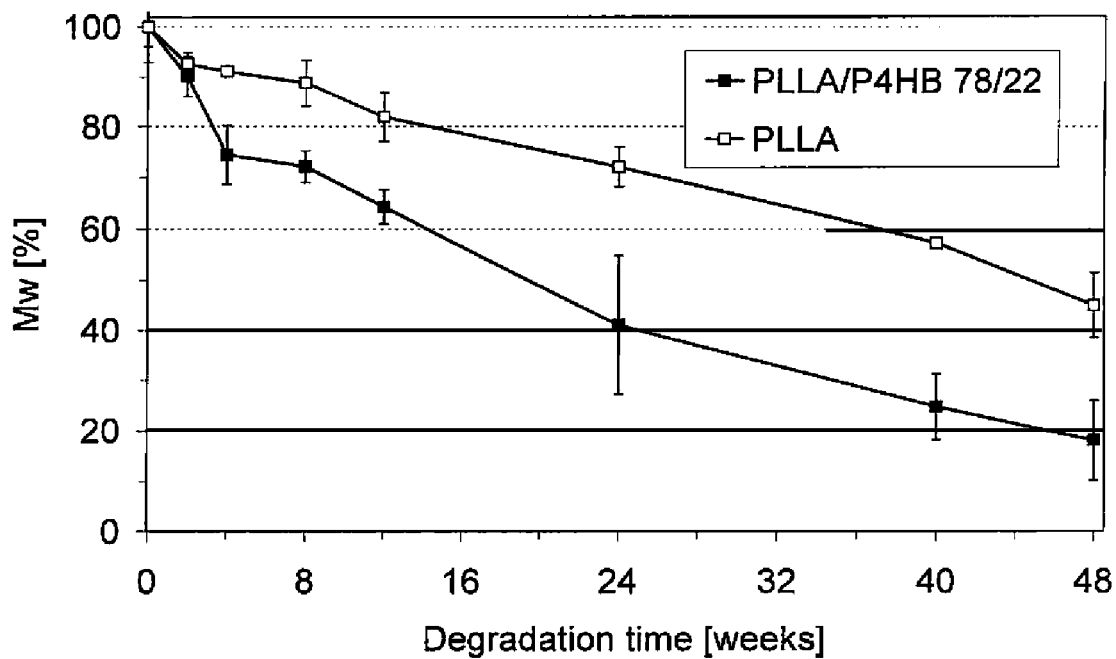
FIG. 3 is a graph showing the accelerated decrease of molecular weight (Mv) of a polymer blend material of high molecular weight PLLA and P4HB with a mass ratio of 78:22% in comparison to pure PLLA as a function of in vitro incubation time in Sorensen buffer (pH=7.4) at 37° C.

Accelerated in Vitro Degradation Behaviour of an Absorbable Peripheral Stent from a Polymer Blend Material of High Molecular Weight PLLA and P4HB Balloon-expandable absorbable peripheral stents with nominal dimensions in the diluted state of 6.0 mm×25 mm were manufactured from a polymer blend of high molecular weight PLLA (Resomer® L214 from Boehringer Ingelheim Pharma), and P4HB (TephaFLEX® biomaterial from Tepha Inc., Mw 300-600K) with a mass ratio of 78/22% or from pure high molecular weight PLLA (Resomer® L214). The stents were deployed with balloon catheters and then incubated in vitro in Sørensen buffer solution at 37° C. to evaluate hydrolytic degradation in vitro After 0/2/4/8/12/24/48 weeks, stents were removed from storage and analyzed by gel permeation chromatography (GPC) to determine molecular weight. FIG. 3 shows the accelerated decrease of molecular weight of the polymer blend material of high molecular weight PLLA and P4HB in comparison to pure PLLA.

Example 9

In Vitro Drug Release Kinetics of Permanent Drug-Eluting Stents with Absorbable Polymeric Coating Matrix and Incorporated Antiproliferative Immunosuppressant Rapamycin Showing the Influence of Base Coat Thickness, and of Top Coat Thickness on the Release Profile A 0.3% w/w solution of P4HB (TephaFLEX® Biomaterial from Tepha, Inc., Mw 300-600K) and the immunomodulator rapamycin of 85:15% w/w in chloroform was prepared. Metallic coronary stents were spray-coated with this solution as a base coat, until a coating layer thickness of 10-20 micrometer was achieved, which is equivalent to a drug content of 1-2 μg per $mm^2$ of stent surface area. The stents were then spray-coated with a 0.3% w/w/ solution of P4HB until a top-coated thickness of 5-15 micrometer was achieved in order to establish different diffusion barriers for retarded drug release. After 24 h storage in vacuo to remove the chloroform, the stents were mounted on standard balloon catheters and afterwards deployed to a nominal diameter of 3.5 mm. The stents were then stored in 2 ml of a 0.9% sodium chloride solution and incubated at 37° C. After different time points, aliquots were taken from the elution medium for analysis of released drug, the elution medium was changed, and the stents were put back to storage. The aliquots were analyzed by HPLC.

Figure 4:
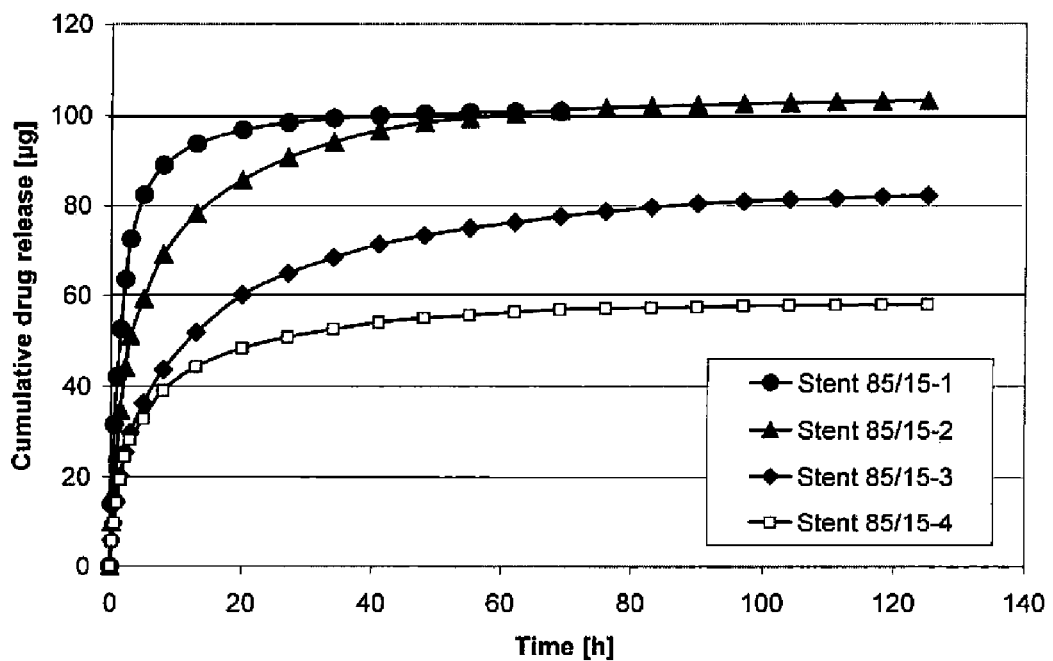
FIG. 4 is a graph showing the in vitro drug release profiles of metallic stents coated with the following different compositions of a P4HB matrix incorporated with the immunomodulator rapamycin as a base coat, and coated with a top coat of pure P4HB as a diffusion barrier for retarded drug release: stent 85:15-1-polymer/drug ratio 85:15 (w/w), base coat thickness=20 µm, no top coats stent 85:15-2-polymer/drug ratio 85:15 (w/w), base coat thickness=20 µm, top coat thickness=5 µm; stent 85:15-3-polymer/drug ratio 85:15 (w/w), base coat thickness=20 µm, top coat thickness=15 µm; stent 85:15-4-polymer/drug ratio 85:15 (w/w), base coat thickness=10 µm, top coat thickness =10 µm.

FIG. 4 displays the in vitro drug release profiles of sample stents, showing the effect of top coat and base coat thicknesses on the drug release profile at a constant drug concentration. The use of a top-coat retarded the drug release (stent 85:15-1 compared to stent 85:15-2). The use of a thicker top-coat retarded the drug release further (stents 85:15-1 and 85:15-2 compared to stent 85:15-3). The use of a thinner base coat reduces the amount of drug released (stent 85:15-1) compared to stent 85:15-1).

Example 10

In Vitro Drug Release Kinetics of Permanent Drug-Eluting Stents with Absorbable Polymeric Coating Matrix and Incorporated Antiproliferative Immunosuppressant Rapamycin Showing the Influence of Drug Content, and of Base Coat Thickness on the Release Profile A 0.3% w/w solution of P4HB (TephaFLEX® biomaterial from Tepha, Inc., Mw 300-600K) and the immunomodulator rapamycin of 85:15% w/w (polymer/drug), or 70:30% w/w, or 40:60% w/w in chloroform was prepared. Metallic coronary stents were spray-coated with either of these solutions as a base coat, until a coating layer thickness of 5-10 micrometer was achieved, which is equivalent to a drug content of 1-2 µg per $mm^3$ of stent surface area. The stents were then spray-coated with a 0.3% w/w solution of P4HB until a top coat thickness of 10 micrometer was achieved in order to establish a diffusion barrier to retard drug release. After 24 h storage in vacuo to remove the chloroform, the stents were mounted on standard balloon catheters and afterwards deployed to a nominal diameter of 3.5 mm. The stents were then stored in 2 ml of a 0.9% sodium chloride solution and incubated at 37° C. After different time points, aliquots were taken from the elution medium, the elution medium was changed, and the stents were put back to storage. The aliquots were analyzed by HPLC.

Figure 5:
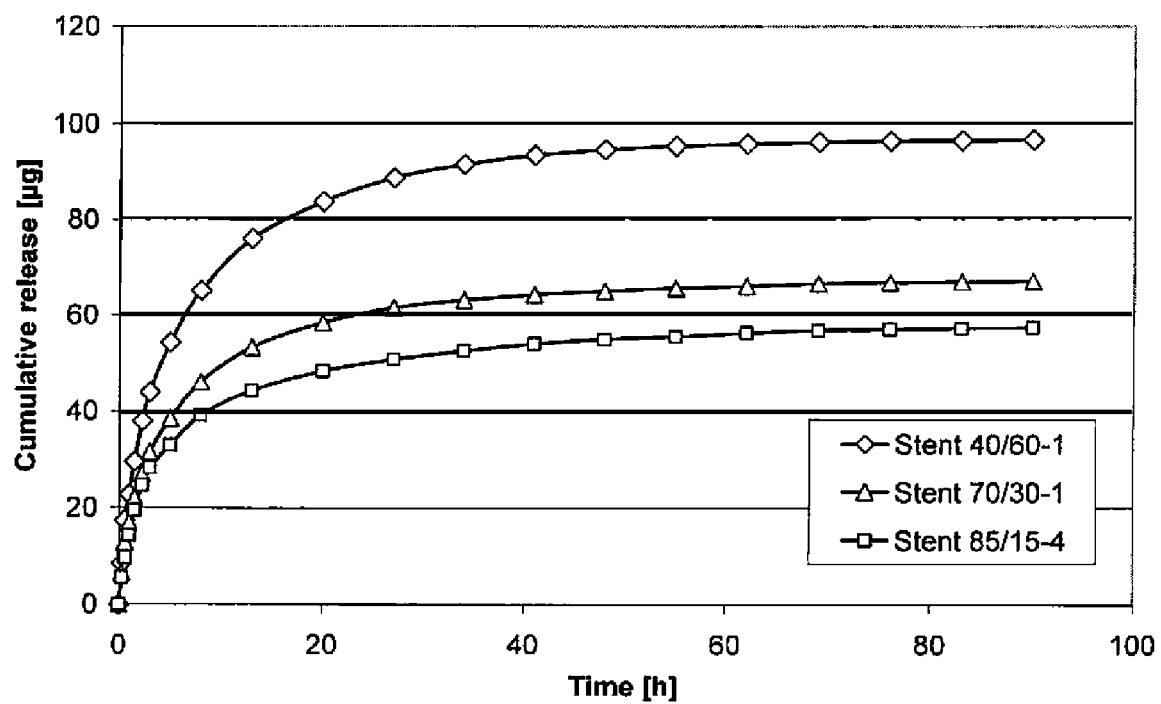
FIG. 5 is a graph showing the in vitro drug release profiles of metallic stents coated with the following different compositions of a P4HB matrix incorporated with the immunomodulator rapamycin as a base coat, and coated with a top coat of pure P4HB as a diffusion barrier for retarded drug release: stent 40:60-1-polymer/drug ratio 40:60 (w/w), base coat thickness=5 µm, top coat thickness=10 µm; stent 70:30-1-polymer/drug ratio 70:30 (w/w), base coat thickness=5 µm, top coat thickness=10 µm; stent 85:15-4-polymer/drug ratio 85:15 (w/w), base coat thickness=10 µm, top coat thickness=10 µm.

FIG. 5 displays in vitro drug release profiles of sample stents, showing the increasing drug release at higher drug concentrations at a constant top-coat thickness. The elution rate and the total amount of drug released increases as the concentration of drug in the basecoat coat increases (stent 85:15-4 compared to stent 70:30-1 and stent 40:60-1).

EXAMPLE 11

Safe Mounting of an Absorbable Coronary Stent onto a Balloon Catheter

Balloon-expandable absorbable stents with an inner diameter of 1.4 mm in the undilated state and a length of 10 mm were manufactured from a polymer blend of high molecular weight PLLA and P4HB (TephaFLEX® biomaterial from Tepha, Inc., Mw 300-600K) by melt extrusion followed by laser cutting. The polymeric stents were mounted without crimping on dedicated balloon catheter systems with nominal dimension of 3.5 mm×10 mm in the dilated state. The balloon catheter system contained an inner support tube in the balloon region underneath the stent to enhance stent retention. The inner support tubing was made from an elastomeric material and provided an interference fit to hold the mounted stent in place. The diameter or durometer of the elastic support tubing could be modified to adjust the resistance of the interference fit and modify the stent retention. The dislodgment force of the stent systems were tested using a universal testing machine.

A mean stent dislodgement force of 2 N, and a maximum dislodgement force of greater than 5 N were measured. Without the inner support tubing, the dislodgment force was less than 0.3 N and would not be suitable for intravascular deployment without some method to hold the stent in place.

Those skilled in the art will recognize, or be able to ascertain using no more than routine experimentation, many equivalents to the specific embodiments of the invention described herein. Such equivalents are intended to be encompassed by the following claims.

We claim:

1. An absorbable biocompatible stent comprising a polymer composition,
    wherein the composition comprises
    (a) one or more polymers selected from the group consisting of poly-4-hydroxybutyrate, copolymers of 4-hydroxybutyrate, and mixtures thereof and
    (b) one or more polymers selected from the group consisting of polylactides, copolymers of lactic acid, and mixtures thereof,
    wherein the composition comprises between 60 and 98% by weight of a polylactide,
    wherein the stent is plastically expandable at normal body temperature, and is of a first diameter sufficient to be retained upon a balloon catheter for placement within a body lumen, and is expandable to a second diameter sufficient to be retained within the body lumen.

2. The stent of claim 1 wherein the stent can be expanded within a body lumen in less than 5 minutes, less than 2 minutes, or less than 1 minute.

3. The stent of claim 2 wherein the stent can be expanded using a balloon pressure of 4-16 bar or less than 9 bar, preferably in less than one minute.

4. The stent of claim 2 wherein the polymeric coating comprises poly-4-hydroxybutyrate or a copolymer containing 4-hydroxybutyrate monomeric units.

5. The stent of claim 1 wherein the stent has a recoil of less than 10% or less than 6%.

6. The stent of claim 1 wherein the stent has a collapse pressure of at least 0.1 bar or between 0.3-0.7 bar.

7. The stent of claim 1 wherein the stent does not creep at 100 mmHg for 7 days.

8. The stent of claim 1 wherein the stent comprises struts and the struts of the stent do not kink or fracture and the stent does not significantly shorten during expansion.

9. The stent of claim 1 comprising struts, wherein the thickness of the struts is less than 300 µm, less than 270 µm, or less than 160 µm.

10. The stent of claim 1 wherein the first diameter of the stent is at least 1 mm, and the second diameter is at least 3 mm.

11. The stent of claim 1 comprising an absorbable polymeric coating, wherein the polymeric coating is plastically expandable at normal body temperature without cracking or delaminating, and is of a first diameter sufficient to be retained upon a balloon catheter for placement within a body lumen, and is expandable to a second diameter sufficient to be retained within the body lumen.

12. The stent of claim 1 wherein the polymer composition comprises between 2 and 40% by weight of a homopolymer or copolymers of 4-hydroxybutyrate.

13. The stent of claim 1 wherein the polymer composition comprises between 5 and 25% by weight of a homopolymer or copolymers of 4-hydroxybutyrate.

14. The stent of claim 1 wherein the polymer composition comprises between 75 and 95% by weight of a polylactide.

15. The stent of claim 1 wherein the polymer composition comprises:
    between 2 and 40% by weight of homopolymer or copolymers of 4-hydroxybutyrate, and
    between 60 and 98% by weight of a polylactide.

16. The stent of claim 15, wherein the polymer composition comprises (a) between 5 and 25% by weight of a homopolymer or copolymer of 4-hydroxybutyrate, and (b) between 75 and 95% by weight of a polylactide.

17. The stent of claim 1 wherein the polymer composition further comprises a plasticizer, preferably present between 0 to 10% by weight of the polymer, most preferably present between 0 and 5% by weight of the polymer.

18. The stent of claim 17 wherein the plasticizer is triethylcitrate.

19. The stent of claim 1 wherein the polymeric composition degrades in less than two years, more preferably in less than one year.

20. The stent claim 1 wherein the molecular weight of the polymeric composition decreases more than 50% in 40 weeks.

21. The stent of claim 1 wherein the stent further comprises a polymeric top coating over the polymeric composition.

22. The stent of claim 21 wherein the polymeric top coating degrades in less than two years, more preferably in less than one year, and most preferably in less than six months.

23. The stent of claim 1 wherein the stent further comprises one or more therapeutic, prophylactic or diagnostic agents.

24. The stent of claim 23 wherein the agent is selected from the group consisting of anti-inflammatory agents, immunomodulators, antiproliferatives, cytostatics, anti-migratory agents, extracellular matrix modulators, vascular healing promoters, endothelialization promoters, anticoagulants, antibiotics, anti-tumor agents, anti-cancer agents, and combinations thereof.

25. The stent of claim 23 wherein the agent is incorporated into the polymer composition by a technique selected from the group consisting of spray coating, dip coating, whirl sintering, and combinations thereof 26. The stent of claim 23 wherein the agent is released from the stent in vivo.

27. The stent of claim 23 wherein the stent comprises one or more diagnostic agents selected from the group consisting of radio-opaque and contrast substances.

28. The stent of claim 1, wherein the stent is suitable for use in a coronary, peripheral, urological, gastroenterological, neurological, esophageal or tracheal procedure.

29. The stent of claim 1, wherein the stent is capable of being sterilized by gamma-irradiation, electron beam, or treatment with ethylene oxide.

30. A method of making the stent of any of claim 1, the method comprising fabricating a tube or stent blank using a technique selected from the group consisting of solution based dip-coating, casting, and combinations thereof or a technique selected from the group consisting of extrusion and injection molding.

31. The method of claim 30 wherein the stent blank consists of one or more fibers, which are fabricated in a melt based process like extrusion or injection molding, and which are optionally reinforced by a drawing process.

32. The method claim 30 wherein the stent is manufactured by laser machining or cutting of a tube or stent blank.

33. The method claim 31 wherein the stent is manufactured by winding, knitting, braiding, weaving or welding of one or several fiber blanks into a tubular stent structure.

34. The method of claim 30 comprising applying an absorbable polymer coating to a tube or stent blank by a technique selected from the group consisting of spray coating, dip coating, and whirl sintering.

35. A method of deploying the stent of any of claim 1, comprising mounting the stent on a delivery system and balloon-expanding the stent inside the body lumen with a balloon pressure of 4 to 16 bar, more preferably less than 9 bar.

36. The method of claim 35 wherein the stent dislodgement force is greater than 1 N.

37. The method of claim 35, wherein the stent is mounted on a delivery system and is self-expanded.

38. A metal stent comprising an absorbable polymeric coating, wherein the polymeric coating comprises
(a) one or more polymers selected from the group consisting of poly-4-hydroxybutyrate, copolymers of 4-hydroxybutyrate, and mixtures thereof and
(b) one or more polymers selected from the group consisting of polylactides. copolymers of lactic acid, and mixtures thereof,
wherein the composition comprises between 60 and 98% by weight of a polyiactide.
wherein the stent coating is plastically expandable at normal body temperature without cracking or delaminating and is of a first diameter sufficient to be retained upon a balloon catheter for placement within a body lumen, and is expandable to a second diameter sufficient to be retained within the body lumen.

39. The stent of claim 38, wherein the polymer coating comprisespoly-4-hydroxybutyrate.

40. The stent of claim 38, wherein the polymer coating comprises a copolymer containing 4-hydroxybutyrate monomeric units.

41. The stent of claim 38, wherein the stent further comprises one or more therapeutic, prophylactic or diagnostic agents.

42. The stent of claim 41, wherein the agent is released from the stent in vivo.

43. The stent of claim 41, wherein the stent comprises one or more diagnostic agents selected from the group consisting of radio-opaque and contrast substances.

44. The stent of claim 41, wherein the agent is selected from the group consisting of anti-inflammatory agents, immunomodulators, antiproliferatives, cytostatics, anti-migratory agents, extraceltular matrix modulators, vascular healing promoters, endothelialization promoters, anticoagulants, antibiotics, anti-tumor agents, anti-cancer agents, and combinations thereof.

45. The stent of claim 41, wherein the therapeutic agent is selected from the group consisting of anti-tumor agents, anti-cancer agents, antibiotic agents, and combinations thereof.

46. The stent of claim 38, wherein the stent is suitable for use in a coronary, peripheral, urological, gastroenterological, neurological, esophageal or tracheal procedure.

* * * * *

UNITED STATES PATENT AND TRADEMARK OFFICE
CERTIFICATE OF CORRECTION

PATENT NO. : 7,618,448 B2
APPLICATION NO. : 11/671632
DATED : November 17, 2009
INVENTOR(S) : Klaus-Peter Schmitz et al.

It is certified that error appears in the above-identified patent and that said Letters Patent is hereby corrected as shown below:

Claim 25, column 17, line 34, replace "thereof" with --thereof.--.
    Claim 30, column 17, line 47, replace "of any of" with --of--.
    Claim 32, column 17, line 57, replace "method claim" with --method of claim--.
    Claim 35, column 18, line 8, replace "of any of" with --of--.
    Claim 38, column 18, line 22, replace "polylactides." with --polylactides,--.
    Claim 38, column 18, line 25, replace "polviactide." with --polylactide,--.
    Claim 39, column 18, line 33, replace "comprisespoly-4-hydroxybutyrate" with --comprises poly-4-hydroxybutyrate--.

Signed and Sealed this
Twenty-first Day of June, 2011

David J. Kappos
*Director of the United States Patent and Trademark Office*